(12) United States Patent
Pretorius

(10) Patent No.: US 6,786,861 B1
(45) Date of Patent: Sep. 7, 2004

(54) DISTENSIBLE SLING FOR URINARY INCONTINENCE

(75) Inventor: Johannes Jacobus Pretorius, 101 Rodene Avenue, Lynnrodene, Pretoria 0040 (ZA)

(73) Assignees: Nicolaas Daniel Lombard Burger (ZA); Rudolf Werner Ottermann (ZA); Adam Jacobus Von Wielligh (ZA); Johannes Jacobus Pretorius (ZA)

( * ) Notice: Subject to any disclaimer, the term of this patent is extended or adjusted under 35 U.S.C. 154(b) by 0 days.

(21) Appl. No.: 09/806,656
(22) PCT Filed: Sep. 30, 1999
(86) PCT No.: PCT/ZA99/00104
§ 371 (c)(1),
(2), (4) Date: May 18, 2001
(87) PCT Pub. No.: WO00/18319
PCT Pub. Date: Apr. 6, 2000

(30) Foreign Application Priority Data

Oct. 1, 1998 (ZA) .............................................. 98/8948

(51) Int. Cl.$^7$ ................................................. A61F 2/00
(52) U.S. Cl. ........................................................ 600/31
(58) Field of Search .............................. 600/29–31, 37; 128/DIG. 25

(56) References Cited

U.S. PATENT DOCUMENTS

| | | | | |
|---|---|---|---|---|
| 4,019,499 A | * | 4/1977 | Fitzgerald | ............ 128/DIG. 25 |
| 4,632,114 A | * | 12/1986 | Todd et al. | .......... 128/DIG. 25 |
| 4,709,690 A | | 12/1987 | Haber | |
| 4,881,939 A | * | 11/1989 | Newman | ............. 128/DIG. 25 |
| 5,078,676 A | | 1/1992 | Bailly | |
| 5,163,897 A | * | 11/1992 | Persky | ................ 128/DIG. 25 |
| 5,593,443 A | * | 1/1997 | Carter et al. | ......... 128/DIG. 25 |
| 6,045,498 A | * | 4/2000 | Burton et al. | ................ 128/898 |
| 6,095,969 A | * | 8/2000 | Karram et al. | ................. 600/29 |

FOREIGN PATENT DOCUMENTS

| EP | 0 650 703 A | 5/1995 |
|---|---|---|
| WO | WO8502993 A | 7/1985 |

* cited by examiner

Primary Examiner—Samuel G Gilbert
(74) Attorney, Agent, or Firm—Akerman Senterfitt (57) ABSTRACT

The invention provides a sling prosthesis (10) for urinary incontinence and also a method of treating urinary incontinence. The sling (10) has a flexible elongate member (12) and a distensible portion (14) and is configured to be inserted dorsally between the urethra and pelvic bone, with ends of the elongate member attachable to retropubic or ischial structures. A valve (18) which is subcutaneously implantable in a labial or scrotal region may be connected via a conduit (16) to the dispensible portion. Fluid is injected via the valve into the distensible portion (14) to that the distensible portion (14) sufficiently constricts the urethra to inhibit undesirable leakage of urine. Fluid can then either be injected into or extracted from the distensible portion in order to alter distension thereof.

15 Claims, 5 Drawing Sheets

DISTENSIBLE SLING FOR URINARY INCONTINENCE

The invention relates to a sling for urinary incontinence and to a method of treating urinary incontinence.

BACKGROUND TO THE INVENTION

In healthy people, muscular tube-like ureters move urine from the kidneys to the bladder, where it is stored until it is convenient to urinate, at which point the urine flows out of the body through the tube-like urethra. A circular muscle, called the sphincter, controls the activity of the urethra.

Stress incontinence is a storage problem in which the urethral sphincter is not able to hold urine. Storage problem may occur as a result of weakened pelvic muscles that support the bladder (seen especially in elderly people), or malfunction of the urethral sphincter. Prior trauma to the urethral area, neurological injury, and some medications may also weaken the urethral closure.

More particularly, an underactive outlet in then may result from a congenital defect or from direct or indirect trauma to the anatomy or physiology of the bladder outlet. Indeed, direct trauma due to prostatectomy is the most common cause of male sphincter weakness.

Stress incontinence may be seen in women who have had multiple pregnancies, pelvic surgery, pelvic prolapse (protrusion of the bladder or urethra into the vaginal space), cystocele, (or rectocele. Additionally, women with low estrogen levels may have stress incontinence due to decreased vaginal muscle tone.

Stress incontinence results in a condition in which patients suffer urine leakage when coughing, sneezing, standing up, lifting objects, or physically exerting themselves. Sufferers may experience not only physical discomfort, but also emotional discomfort. Many people affected by loss of bladder control isolate themselves for fear of embarrassment and ridicule, and the condition is often connected to a loss of self-esteem, with many sufferers being too embarrassed to report the condition or seek medical treatment. Adults also often find employment difficult or impossible because of these factors.

While many sufferers of stress incontinence simply wear a catheter or adult diaper, the applicant is aware of many different surgical procedures that may be used to treat incontinence. Some of the more common procedures performed to treat urinary incontinence include bladder neck suspension or sling procedures, periurethral bulking injections (for example, collagen injections around the urethra injections of other material and injections of balloon-like structures), anterior vaginal repair or implantation of an artificial urinary sphincter.

Many of these procedures have potentially serious complications, for example, potential complications that can occur alter a collagen injection include infection, urine retention, and temporary erectile dysfunction in men. Some people may also have a potentially serious allergic reaction to collagen. Some of the procedures also require substantial invasive surgery, which is not only expensive but is also potentially harmful for the patient undergoing the surgery. Invasive surgery is again required if the continence of the patient later changes, if the original procedure was insufficient to properly treat the incontinence or if infection necessitates removal of the device. Furthermore, sometimes discomfort experienced by patients having, for example artificial urinary sphincters, is not negligible. Apart from the above factors, the products and procedures are expensive, thereby often limiting the treatment available to many patients.

In the sling procedure mentioned above, a piece of abdominal tissue (fascia) or synthetic material is placed underneath the urethra like a hammock or sling to support and compress it, thus inhibiting urine leakage during stress manoeuvres. The various sling procedures performed all involve placing a sling under the urethrovesical junction and anchoring it to retropubic or abdominal structures or both. These procedures have traditionally been performed on mostly female patients, where the sling is placed between the urethra and vaginal wall.

Severe complications, many of which are directly attributable to local effects of the sling (i.e. infection, erosion of the sling, nonhealing of the vaginal wall in women, abscess and vesicovaginal fistula in women) have been observed. Other possible complications include urinary retention and new onset of irritative voiding symptoms.

A need therefore exists to provide an affordable and simplified device and procedure for treating urinary stress incontinence, which reduces the possibility of complications arising, requires less invasive surgery and which is easier to adjust, especially in men.

SUMMARY OF THE INVENTION

Accordingly, according to a first embodiment of the invention there is provided a prosthesis for treating urinary incontinence, the prosthesis including:

a flexible elongate member; and a distensible portion.

The distensible portion may be located an a surface of the elongate member. The prosthesis may include a conduit, typically a flexible pipe, in flow communication with the distensible portion. A valve means connected to an end of the conduit remote from the distensible portion may be provided, the valve means being in flow communication with the distensible portion.

At least one ridge may be located on an inner surface of the distensible portion. Similarly, at least one longitudinal or spiral ridge may be located along at least a portion of the length of an inner surface of the conduit.

The valve means may be sized and configured to permit subcutaneous implantation thereof in a labial region of a female patient, or in a scrotum of a male patient. The valve means typically includes a housing, a layer of resiliently deformable material; and a protection means for protecting the conduit from penetration by a sharp-object. The resiliently deformable material may be self-scaling, for example, the material may be a silicone rubber. An outer surface of the valve means may contain grooves or ridges.

The sharp object from which the protection means protects the conduit may be a needle, more particularly, a syringe needle. The protection means may be a cone-shaped plate having perforations to permit fluid flow therethrough.

The elongate member, distensible portion and conduit may be manufactured from bio-compatible materials. Similarly, the valve means may be covered with a bio-compatible material According to a second embodiment of the invention there is provided a method for surgically treating urinary incontinence, the method including the following steps:

inserting a prosthesis dorsally between the urethra and pelvic bone the prosthesis including a flexible elongate member and a distensible portion, and securing either end of the elongate member to retropubic or ischial structures such that the distensible portion is positioned between the urethra and pelvic bone.

The prosthesis may be a prosthesis substantially of the type described above.

The prosthesis may be positioned such that the distensible portion is located between the urethra and the elongate member, and the elongate member is located between the pelvic bone and the distensible portion. The ends of the elongate member are preferably attached to left and right inferior pubic rami using non-absorbable sutures. The valve means may be subcutaneously implanted in a labial region of a female patient, or in a scrotum of a male patient.

The method may further include the step of distending the distensible portion by injecting fluid, preferably a fluid containing radio-opaque dye, into the distensible portion through the valve means in order to increase pressure exerted by the prosthesis on the urethra. The distensible portion may be distended until the pressure is sufficient so as to substantially constrict the urethra. Fluid may also be extracted from the distensible portion through the valve means so as to decrease the pressure exerted by the prosthesis on the urethra.

DESCRIPTION OF THE DRAWINGS

The invention will now be described further, by way of non-limiting example, with reference to the accompanying drawings.

In the drawings.

Referring to the drawings, reference numeral 10 generally indicates a prosthesis in accordance with the invention.

Figure 1A:
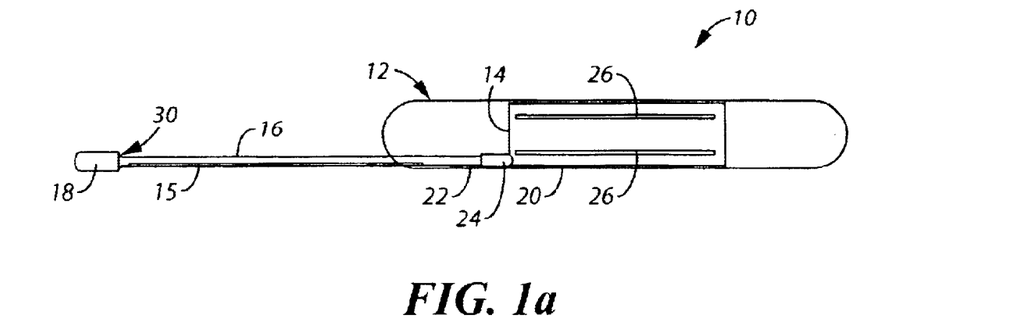
FIG. 1a shows a plan view of a prosthesis for use in treatment of urinary incontinence according to the present invention including a conduit having a longitudinal ridge.
Figure 1B:
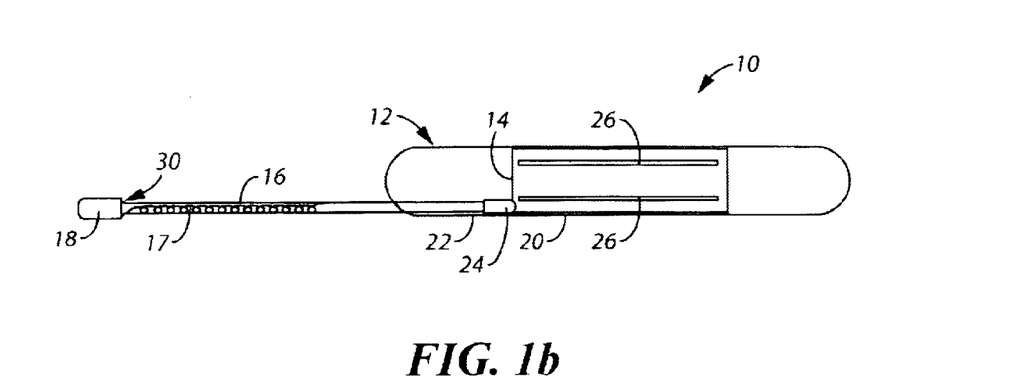
FIG. 1b shows a plan view of a prosthesis for use in treatment of urinary incontinence according to the present invention including a conduit having a spiral ridge.
Figure 2:
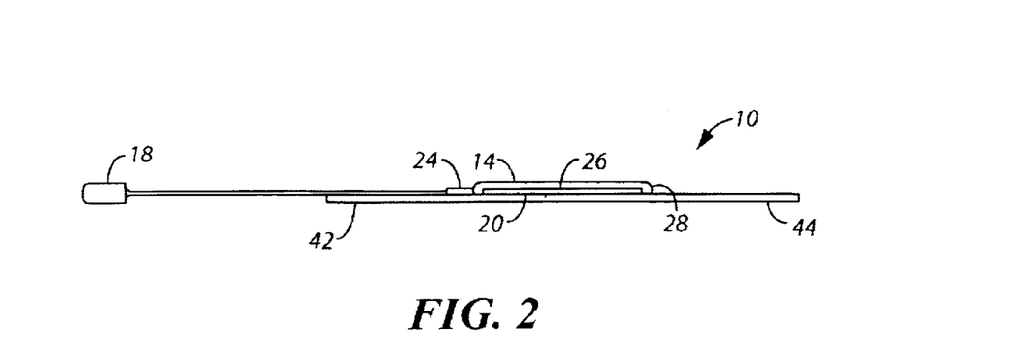
FIG. 2 shows a front view of the prosthesis of FIG. 1.

In FIGS. 1 and 2, the prosthesis 10 has a flexible elongate member 12, a distensible portion 14, a conduit in the form of a flexible pipe 14 and a valve means in the form of a valve 18.

The elongate member 12 is in the form of a fibre-reinforced sling 12 manufactured from silicone impregnated nylon fibre. The distensible portion 14 is in the form of a balloon 14 bonded to a surface 20 of the sling 12.

One end 22 of the pipe 16 is attached to the balloon 14 so as to be in fluid flow communication therewith. A collar 24 is provided to facilitate bonding of the pipe 16 to the balloon 14. Longitudinal ridges 26 are located on an inner wall 28 of the balloon 14 to inhibit blockage of the balloon 14 due to external pressure when the balloon 14 is in an undistended state.

Moulded longitudinal ridges 15 (as shown in FIG. 1a) or spiral ridges 17 (as shown in FIG. 1b) in the pipe 16 inhibit kinking of the pipe 16 and thereby prevent potential blockages in the pipe 16 which could be caused if the pipe 16 were to kink. The longitudinal ridges also inhibit blockage to the pipe 16 which may be caused by external pressures exerted on the pipe 16 after implantation in a patient.

Figure 3:
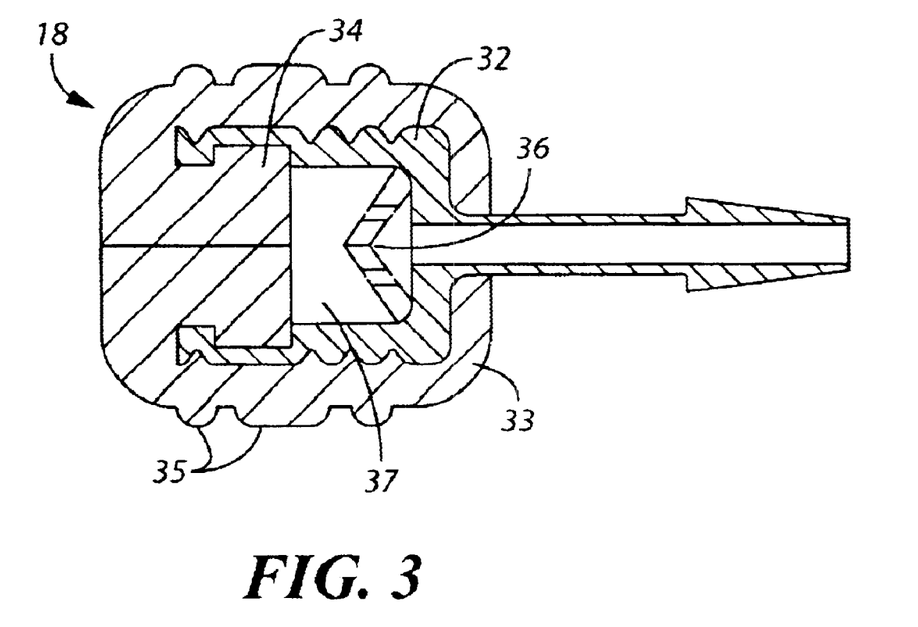
FIG. 3 shows a sectioned side view of a valve of the prosthesis of FIG. 1.

Referring also to FIG. 3, end portion 30 of the flexible pipe 16 is attached to the valve 18. The valve 18 has a stainless steel housing 32; a layer of resiliently deformable elastic polymeric material 34 of the silicone rubber or sealant type; and a protection means in the form of a substantially conical plate 36. The silicone rubber material 34 forms a plug 34 in the valve body 37. The plate 36 is perforated to allow fluid flow therethrough while inhibiting larger solid material from passing through the valve 18 into the pipe 16. Ridges 35 are located on an outer surface of the housing 32. The housing 32 and silicone plug 34 are encapsulated with silicone rubber 33 to provide biocompatibility of the valve 18 and also to insulate the valve 18 in the event that the valve 18 develops a leak.

Figure 4:
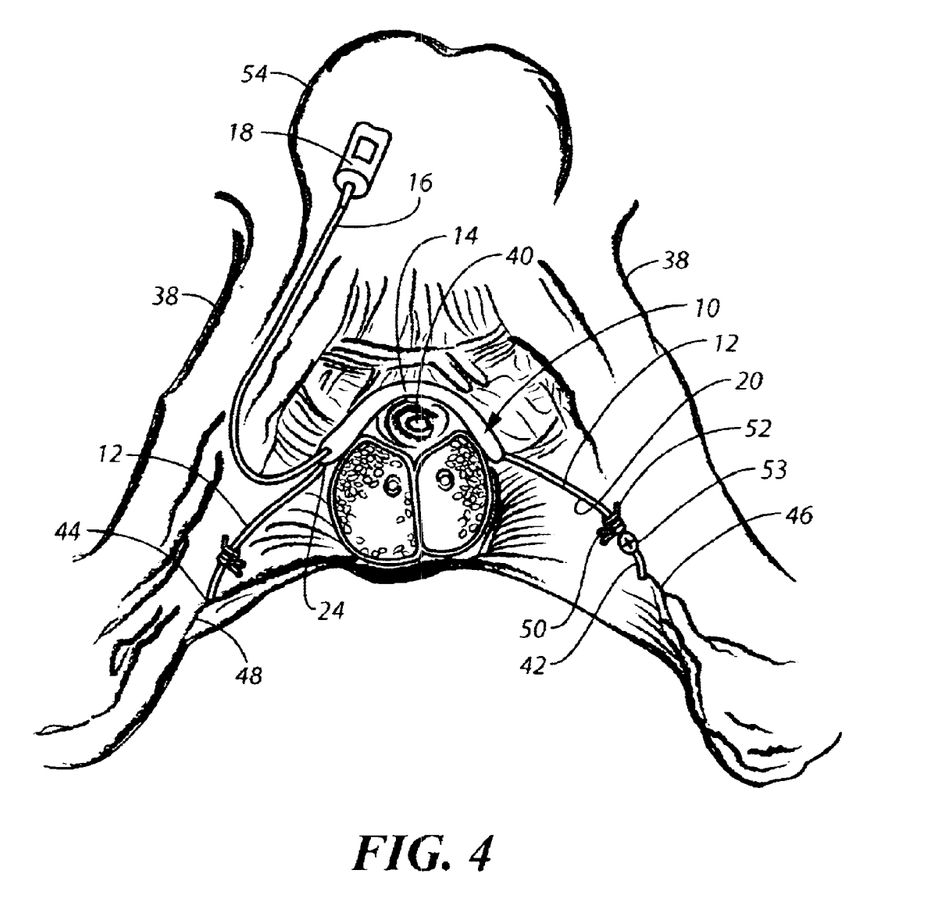
FIG. 4 shows a front partially sectioned view of the prosthesis of FIG. 1 in a male patient.
Figure 5:
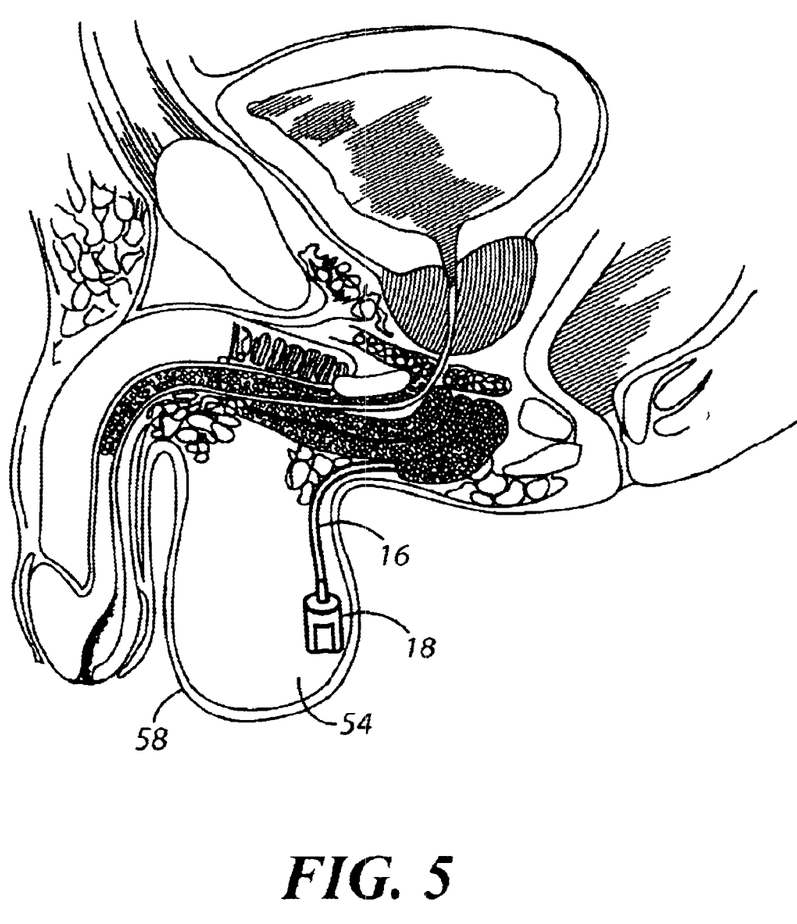
FIG. 5 shows a side view of the prosthesis of FIG. 4.
Figure 6:
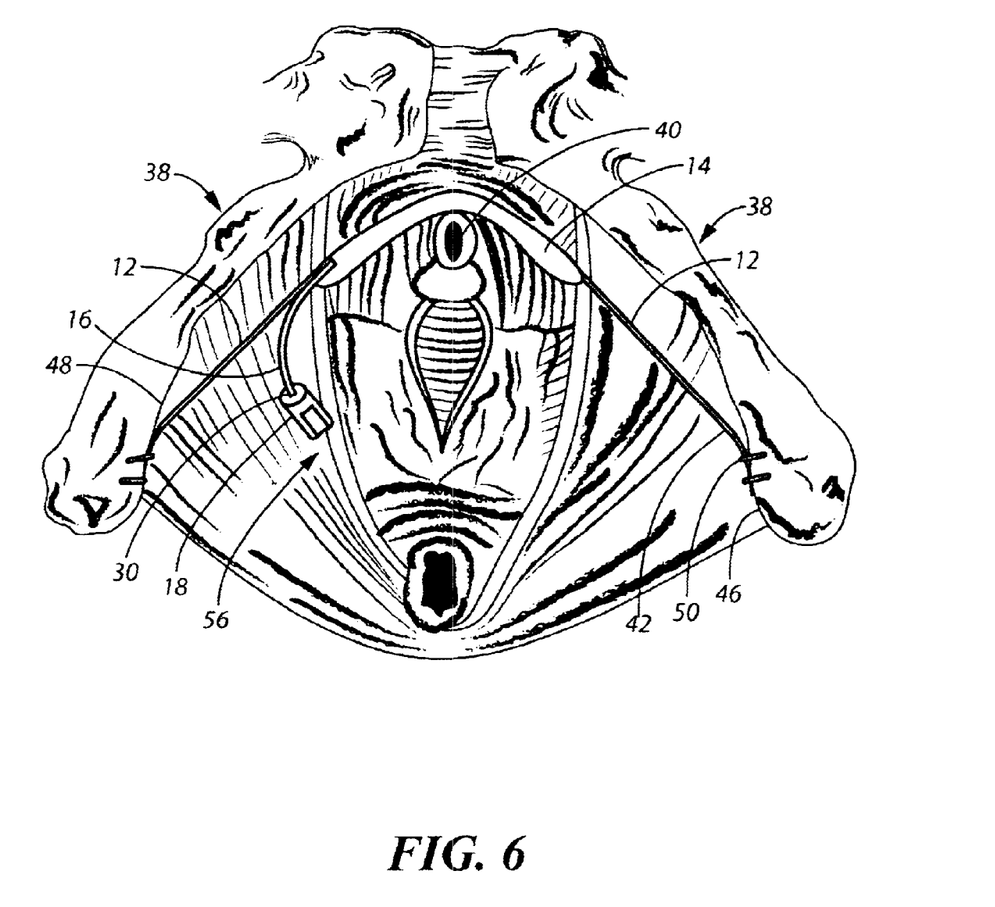
FIG. 6 shows a front sectioned view of the prosthesis of FIG. 1 in a female patient.

Referring now to FIGS. 4 to 6, the prosthesis 10 is permanently implanted in a patient whilst the patient is under anaesthesia. The sling 12 is cut to a required size to permit it suitable fit for implantation and attachment to the pelvic bone 38. The prosthesis 10 is inserted dorsally between the patient's urethra 40 and pelvic bone 38 such that the balloon 14 is positioned between, the urethra 40 and the sling surface 20, with the sling, 12 located against the pelvic bone 38. End portions 42 and 44 of the sling 12 are secured to the patient's left and right inferior pubic rami 48 and 48, respectively, in order to maintain the balloon 14 in its desired position. Non-absorbable sutures 50, which run through the fibre-reinforced sling 12, are used to secure the prosthesis 10 to the pubic rami 46 and 48. Surgical staples 52 and screws 63 are in some instances additionally used.

The flexible pipe 16 and valve 18 are then routed to a scrotum 54 if the patient is male or to a labium 56 if the patient is female, and are subcutaneously implanted so that the implanted valve 18 remains easily accessible after completion of the implantation procedure. The ridges 35 moulded on the outer surface of the housing 22 permit easy attachment of the valve 18 onto the tissue underlying the skin 58 by means of non-soluble sutures (not shown). This also inhibits the valve 18 from becoming displaced from the implantation location. After implantation of the prosthesis 10 is complete, air inside the balloon 14 is extracted and the operating wound is closed.

Approximately four weeks after the above procedure, the balloon 14 is systematically distended with a fluid, typically distilled water, containing a radio opaque dye. The position of the valve 18 is located underneath the skin 58 of the patient and the radio opaque dye is injected into the valve 18, using a syringe and needle (not shown). The needle penetrates the silicone sealant plug 34 in the stainless steel housing 32. The needle is unable to penetrate the conical plate 36, which serves to protect the pipe 16 from accidental puncture by the needle should too much pressure be applied when inserting the needle Into the valve 18. Fluid from the syringe is then injected into the valve 18, from where the fluid flows through the perforations in the plate 36 into the pipe 16 and balloon 14.

As the fluid flows into the balloon 14, the balloon 14 distends and exerts pressure on the pelvic bone 38 and urethra 40. This pressure blocks the urinary pathway by forming an artificial obstruction in the urethra 40. This obstruction simulates the function of the sphincter (not shown), thus inhibiting leakage of urine from the bladder (also not shown). Radiography is used during the inflation procedure to enable the practitioner conducting the procedure to ascertain when the urethra 40 becomes obstructed. The syringe needle is then removed from the valve 18 and the silicone sealant 34 seals the perforation created by the needle.

The balloon pressure required to sufficiently obstruct the urethra 40 and thus inhibit leakage of urine varies from patient to patient. Typically 3 ml to 6 ml, and more particularly 4 ml to 5 ml of fluid is required for the balloon 14 to he sufficiently distended to obstruct the urethra 40. The pressure in the balloon 14 can easily be altered by injecting or extracting the fluid into or from the valve 18 located underneath the skin 58. This can be repeated until such time as the correct pressure is attained.

Similarly, if the continence of the patient later changes, for example due to weight change or other physical changes, the amount of fluid in the balloon can easily be increased or decreased in the manner described above.

While the balloon 14 must be sufficiently distended to inhibit urine leakage, it is also important that the balloon 14 not exert too match pressure on the urethra 40 so that normal urination becomes impossible or difficult. When the patient wishes to urinate, the bladder detrusor muscles contract, causing an increase in bladder pressure. If the patient also exerts pressure on the lower abdominal organs by pressing down on the abdominal area slightly, the combination of these pressures causes the urethra 40 to move down and away from the balloon 14. Less pressure is this exerted on the urethra 40 by the balloon 14 and urine should therefore be able to pass through the obstruction, resulting in normal controlled urination. If normal urination is not possible in this way, then the balloon 14 has been over-distended, and fluid can be extracted therefrom.

Although the above described surgical procedure has thus far been experimentally performed on male patients only, the procedure and prosthesis is also suitable for use in female patients. In particular, the positioning of the sling 12 and balloon 14 between the urethra 40 and pelvic bone 38, rather than between the urethra 40 and vaginal wall 39, is advantageous in that the risk of damage and/or sepsis of the vaginal wall 39 as a result of friction between the sling 12 and vaginal wall 39 is removed.

In the trials conducted so far, each patient had prior to the implantation of the prosthesis been required to wear a catheter. After implantation of the prosthesis, all the patients showed an improvement in continence, and correspondingly all the patients reported a cessation of incontinence.

All materials used are bio-compatible and inert due to the permanent nature of the prosthesis in the body. The balloon, sling and pipe are manufactured from a two part Bayer Siloprene Liquid Silicone Rubber™ (LSR Grade 40) system. The Siloprene LSR™ grade offers good mechanical strength, flexibility and moulding properties. The materials comply with US Pharmacopoeia XXII, Class VI requirements as well as the requirements set out by the American Food and Drug Administration. The stainless steel insert used for the valve housing and plate is grade 316 L, commonly used in surgical applications.

The invention is not limited to the precise constructional details as herein described. For example, the prosthesis may be manufactured from any suitable bio-compatible material and the valve may be differently configured.

The applicant believes that the invention is advantageous in that it provides a prosthesis for the treatment of stress incontinence which is externally adjustable if the continence of the patient changes, requires less invasive surgery than alternative products and procedures, and is less expensive than alternatives. Furthermore, the costs of the procedure to implant the prosthesis are further reduced because of the reduced operating time required for surgery. The prosthesis is also anatomically designed so that little or no discomfort is experienced by a patient in whom the prosthesis is implanted.

What is claimed is:

1. A urinary incontinence prosthesis including:

a flexible elongate member which is configured to extend between left and right retropubic or ischial structures of a patient when the ends of the elongate member are secured to the respective retropubic or ischial structure; and a distensible portion which is positioned on the elongate member so that in use the distensible portion presses on one side of the urethra so as to apply a pressure sufficient to close the urethra and inhibit unintended passage of urine through the urethra, wherein the prosthesis is configured to form an inverted sling when inserted between the urethra and pelvic bone and the ends of the elongate member are attached to the retropubic or ischial sutures.

2. A prosthesis as claimed in claim 1, wherein distension of the distensible portion is alterable.

3. A prosthesis as claimed in claim 1, which further includes a conduit in flow communication with the distensible portion; and a value means connected to an end of the conduit remote from the distensible portion, the valve means being in flow communication with the conduit and therefore also with the distensible portion.

4. A prosthesis as claimed in claim 3, wherein at least one longitudinal ridge is located along at least a portion of the length of an inner surface of the conduit.

5. A prosthesis as claimed in claim 3, wherein at least one spiral ridge runs along the length of an inner surface of the conduit.

6. A prosthesis as claimed in claim 3, wherein the valve means is sized and configured to permit subcutaneous implantation thereof in a labial region.

7. A prosthesis as claimed in claim 3, wherein the valve means is sized and configured to permit subcutaneous implantation thereof in a scrotum.

8. A prosthesis as claimed in claim 1, wherein at least one ridge is located on an inner surface of the distensible portion.

9. A method for surgically treating urinary incontinence, the method including the following step:

securing one end of a flexible elongate member of a prosthesis to a left retropubic or ischial structure of a patient and securing another end of the elongate member to a right retropubic or ischial structure so that a distensible portion of the prosthesis positioned on the elongate member is in contact with one side of the urethra of the patient at least when the distensible portion is distended wherein the prosthesis is positioned above the urethra to form a slink.

10. A method as claimed in claim 9, wherein the prosthesis is positioned between the urethra and pelvic bone such that the prosthesis forms an inverted sling above the urethra.

11. A method as claimed in claim 9, wherein the urethra is positioned between the prosthesis and pelvic bone such that the prosthesis, when distended, pinches the urethra between the prosthesis and the pelvic bone thereby to inhibit flow through the urethra.

12. A method as claimed in claim 10, which further includes the step of distending the distensible portion so that sufficient pressure is applied to the urethra so as to close the urethra and inhibit unintended passage of urine through the urethra.

13. A method as claimed in claim 11, which further includes the step of distending the distensible portion so that sufficient pressure is applied to the urethra so as to close the urethra and inhibit unintended passage of urine through the urethra.

14. A method as claimed in claim 12, wherein the pressure applied by the prosthesis to the urethra is adjustable by adjusting the distension of the distensible portion by either injecting fluid into or extracting fluid from the distensible portion through a valve which is subcutaneously implanted into a scrotum or labial region and which is in flow communication with the distensible portion.

15. A method as claimed in claim 13, wherein the pressure applied by the prosthesis to the urethra is adjustable by adjusting the distension of the distensible portion by either injecting fluid into or extracting fluid from the distensible portion through a valve which is subcutaneously implanted into a scrotum or labial region and which is in flow communication with the distensible portion.

* * * * *

UNITED STATES PATENT AND TRADEMARK OFFICE
CERTIFICATE OF CORRECTION

PATENT NO. : 6,786,861 B1
DATED : September 7, 2004
INVENTOR(S) : Pretorius

It is certified that error appears in the above-identified patent and that said Letters Patent is hereby corrected as shown below:

Column 1,
Line 19, replace "then" with -- men --.
Line 27, delete "(".
Line 47, insert a comma after "urethra".

Column 2,
Line 29, replace "an" with -- on --.
Line 43, replace the comma after "housing" with a semicolon.
Line 45, replace "sharp-object" with -- sharp object --.
Line 56, add a period after "material".
Line 61, insert a comma after "bone".
Line 62, replace the comma after "portion" with a semicolon.

Column 3,
Line 47, replace "14" with -- 16 --.

Column 4,
Line 22, delete the comma after "sling".
Line 29, replace "63" with -- 53 --.
Line 52, replace "Into" with -- into --.

Column 5,
Line 5, replace "he" with -- be --.
Line 22, replace "this" with -- thus --.

UNITED STATES PATENT AND TRADEMARK OFFICE
CERTIFICATE OF CORRECTION

PATENT NO.    : 6,786,861 B1
DATED         : September 7, 2004
INVENTOR(S)   : Pretorius It is certified that error appears in the above-identified patent and that said Letters Patent is hereby corrected as shown below:

<u>Column 6,</u>
Line 17, replace "sutures" with -- structures --.
Line 51, replace "slink" with -- sling --.

Signed and Sealed this

Fourteenth Day of March, 2006

JON W. DUDAS
*Director of the United States Patent and Trademark Office*